(12) United States Patent
Yamamoto et al.

(10) Patent No.: US 10,364,415 B2
(45) Date of Patent: Jul. 30, 2019

(54) 1,4-DIOXANE-DEGRADING BACTERIA CULTURE METHOD, MEDIUM, AND 1,4-DIOXANE TREATMENT METHOD USING 1,4-DIOXANE-DEGRADING BACTERIA

(71) Applicants: TAISEI CORPORATION, Shinjuku-ku, Tokyo (JP); OSAKA UNIVERSITY, Suita-shi, Osaka (JP); SCHOOL JURIDICAL PERSON KITASATO INSTITUTE, Minato-ku, Tokyo (JP)

(72) Inventors: Norifumi Yamamoto, Tokyo (JP); Yuji Saito, Tokyo (JP); Michihiko Ike, Suita (JP); Masashi Kuroda, Suita (JP); Kazunari Sei, Sagamihara (JP); Daisuke Inoue, Sagamihara (JP)

(73) Assignees: TAISEI CORPORATION, Tokyo (JP); OSAKA UNIVERSITY, Osaka (JP); SCHOOL JURIDICAL PERSON KITASATO INSTITUTE, Tokyo (JP)

( * ) Notice: Subject to any disclaimer, the term of this patent is extended or adjusted under 35 U.S.C. 154(b) by 0 days.

(21) Appl. No.: 15/517,146

(22) PCT Filed: Oct. 7, 2015

(86) PCT No.: PCT/JP2015/078476
§ 371 (c)(1),
(2) Date: Apr. 5, 2017

(87) PCT Pub. No.: WO2016/056592
PCT Pub. Date: Apr. 14, 2016

(65) Prior Publication Data
US 2017/0306290 A1    Oct. 26, 2017

(30) Foreign Application Priority Data

Oct. 9, 2014  (JP) ................................ 2014-207776
Mar. 5, 2015  (JP) ................................ 2015-043804

(51) Int. Cl.
| | |
|---|---|
| C12N 1/20 | (2006.01) |
| B09C 1/10 | (2006.01) |
| C02F 3/00 | (2006.01) |
| C02F 3/34 | (2006.01) |
| C12N 1/32 | (2006.01) |
| C12R 1/01 | (2006.01) |
| C12R 1/32 | (2006.01) |
| C12N 1/38 | (2006.01) |

(52) U.S. Cl.
CPC .................. *C12N 1/20* (2013.01); *B09C 1/10* (2013.01); *C02F 3/00* (2013.01); *C02F 3/34* (2013.01); *C12N 1/32* (2013.01); *C12N 1/38* (2013.01); *C12R 1/01* (2013.01); *C12R 1/32* (2013.01)

(58) Field of Classification Search
CPC ....................................................... B09C 1/10
See application file for complete search history.

(56) References Cited

U.S. PATENT DOCUMENTS 7,166,457 B1    1/2007   Hernandez et al.

FOREIGN PATENT DOCUMENTS

| EP | 1748076 A1 | 1/2007 |
| JP | 2003513781 A | 4/2003 |
| JP | 2008306939 A | 12/2008 |

OTHER PUBLICATIONS

Fincher et al., Applied and Environmental Microbiology, 1962, 10:542-547.*
Coleman et al., Soluble di-iron monooxygenase gene diversity in soils, sediments and ethane enrichments, Environ. Microbiol., 2006, pp. 1228-1239, 8(7).
Grostern et al., Glyoxylate metabolism is a key feature of the metabolic degradation of 1,4-dioxane by Pseudonocardia dioxanivorans strain CB1190, Appl. Environ. Microbiol., Feb. 10, 2012, pp. 3298-3308, 78(9).
International Search Report (ISR) dated Dec. 1, 2015, issued for International application No. PCT/JP2015/078476.
Kosaka et al., The effects of the co-existing compounds on the decomposition of micropollutants using the ozone/hydrogen peroxide process, Water Sci.Technol., 2000, pp. 353-361, vol. 42.
Mahendra et al., Kinetics of 1,4-dioxane biodegradation by monooxygenase-expressing bacteria, Environ. Sci. Technol., Jul. 25, 2006, pp. 5435-5442, 40(17).
Masuda et al., Biodegradation of tetrahydrofuran and 1,4-dioxane by soluble diiron monooxygenase in *Pseudonocardia* sp. strain ENV478, J. Mol. Microbiol. Biotechnol, Nov. 6, 2012, pp. 312-316, 22(5).
McClay K. et al., Biodegradation of bis(2-chloroethyl) ether by *Xanthobacter* sp. strain ENV481, Appl. Environ. Microbiol., Nov. 2007, p. 6870-6875, vol. 73, No. 21.
Notification Concerning Transmittal of International Preliminary Report on Patentability (PCT/IB326) and Notification of Transmittal of Translation of the International Preliminary Report on Patentability (PCT/IB/338) dated Apr. 20, 2017, with International Preliminary Report on Patentability (PCT/IB/373) and Written Opinion of the International Searching Authority (PCT/ISA/237), for corresponding international application PCT/JP2015/078476.
Parales R.E., et al., Degradation of 1,4-dioxane by an actinomycete in pure culture, Appl. Environ. Microbiol., Dec. 1994, p. 4527-4530, vol. 60, No. 12.

(Continued)

*Primary Examiner* — Bin Shen
(74) *Attorney, Agent, or Firm* — Law Office of Katsuhiro Arai

(57) ABSTRACT

To provide an effective 1,4-dioxane-degrading bacteria culture method. Provided is a 1,4-dioxane-degrading bacteria culture method in which 1,4-dioxane-degrading bacteria are propagated using a medium containing diethylene glycol.

6 Claims, 5 Drawing Sheets

(56) References Cited

OTHER PUBLICATIONS

Sei et al., Challenge for biotreatment of groundwater contaminated with 1,4-dioxane by 1,4-dioxane-degrading bacteria, J. Water and Waste, 2011, 555-560, vol. 53, No. 7.
Steffan Robert J., et al., Biodegradation of 1,4-Dioxane, SERDP, Aug. 1, 2007, p. 1-103, ER-1422.
Extended European Search Report (EESR) dated Jun. 20, 2018, issued for European counterpart patent application No. EP15848739.7.
Mochida et al., Toxicity of ethylene glycol diethylene glycol and propylene glycol to human cells in culture, Bulletin of Environmental Contamination and Toxicology, 1987, 151-153, vol. 38, No. 1.
Sei et al., Isolation and characterization of bacterial strains that have high ability to degrade 1,4-dioxane as a sole carbon and energy source, Biodegradation, Dec. 13, 2012, 665-674, vol. 24, No. 5.
Vorapat et al., Biosynthesis of Natural-Synthetic Hybrid Copolymers: Polyhydroxyoctanoate-Diethylene Glycol, Biomacromolecule, Mar. 1, 2004, 643-649, vol. 5, No. 2.

\* cited by examiner

[FIG. 1]
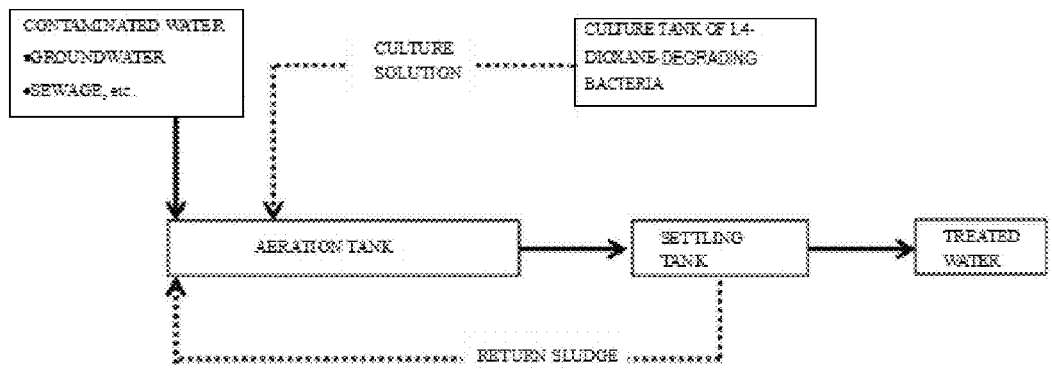
[FIG. 2]
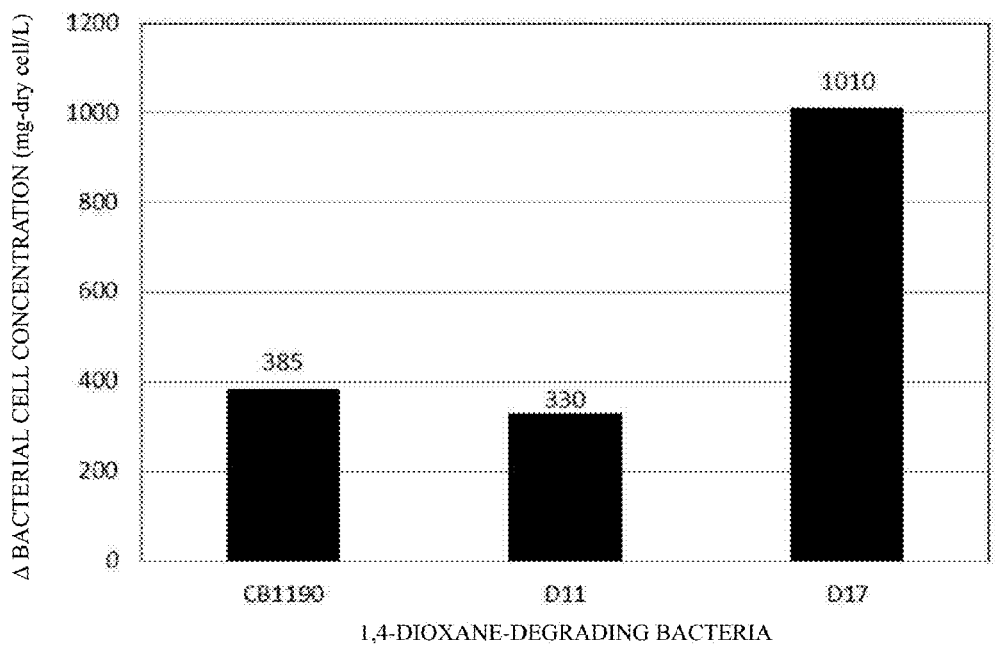

[FIG. 3]
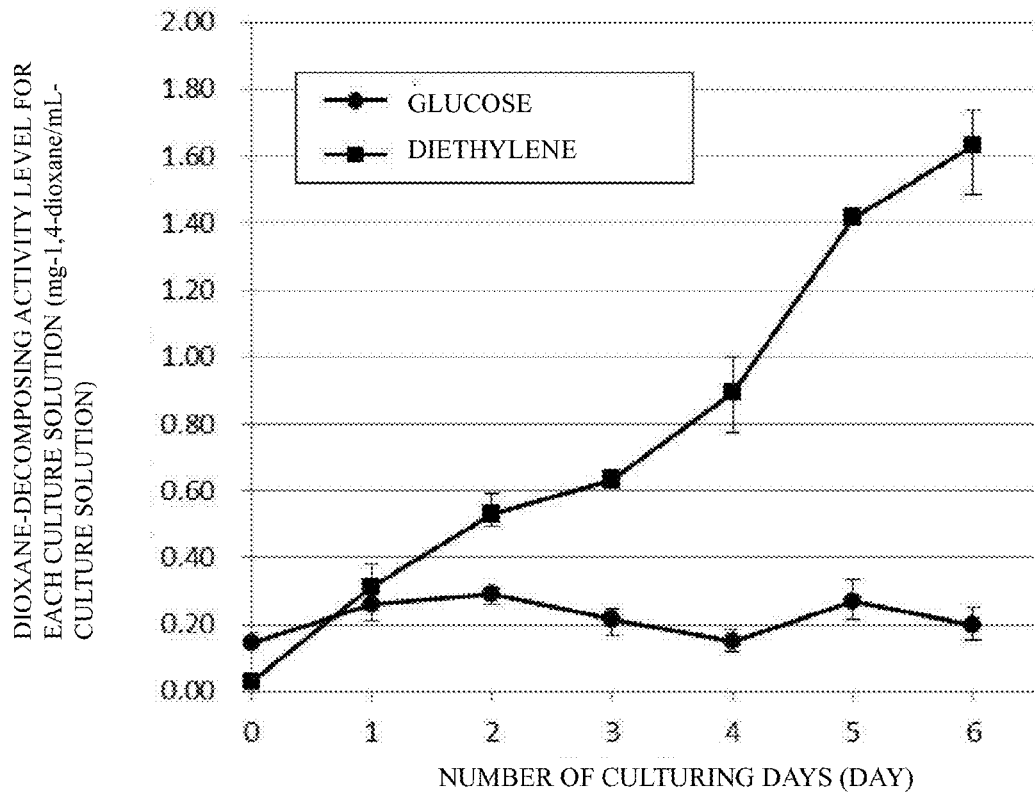
[FIG. 4]
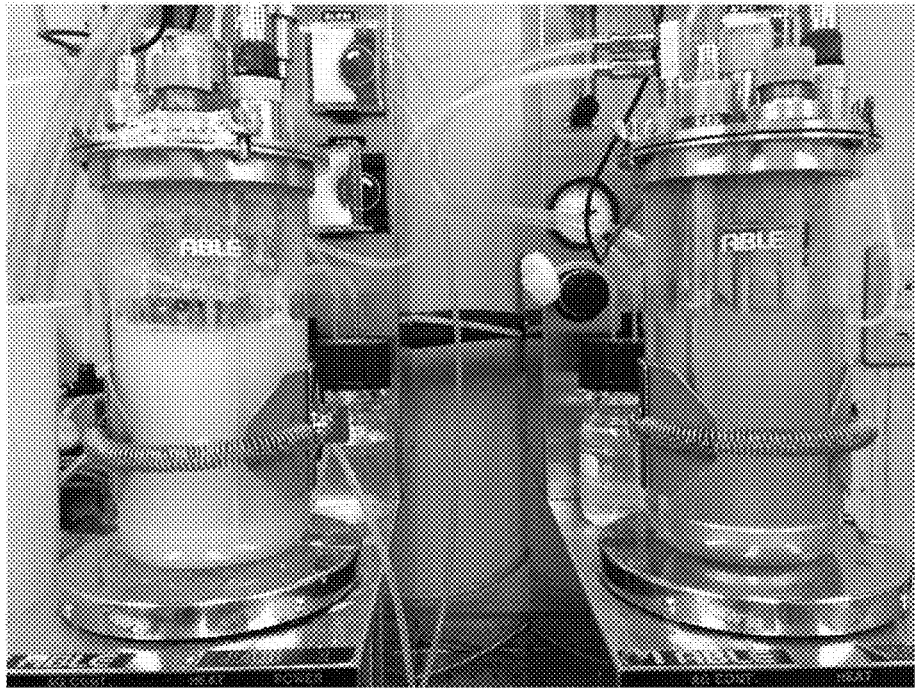

[FIG. 5]
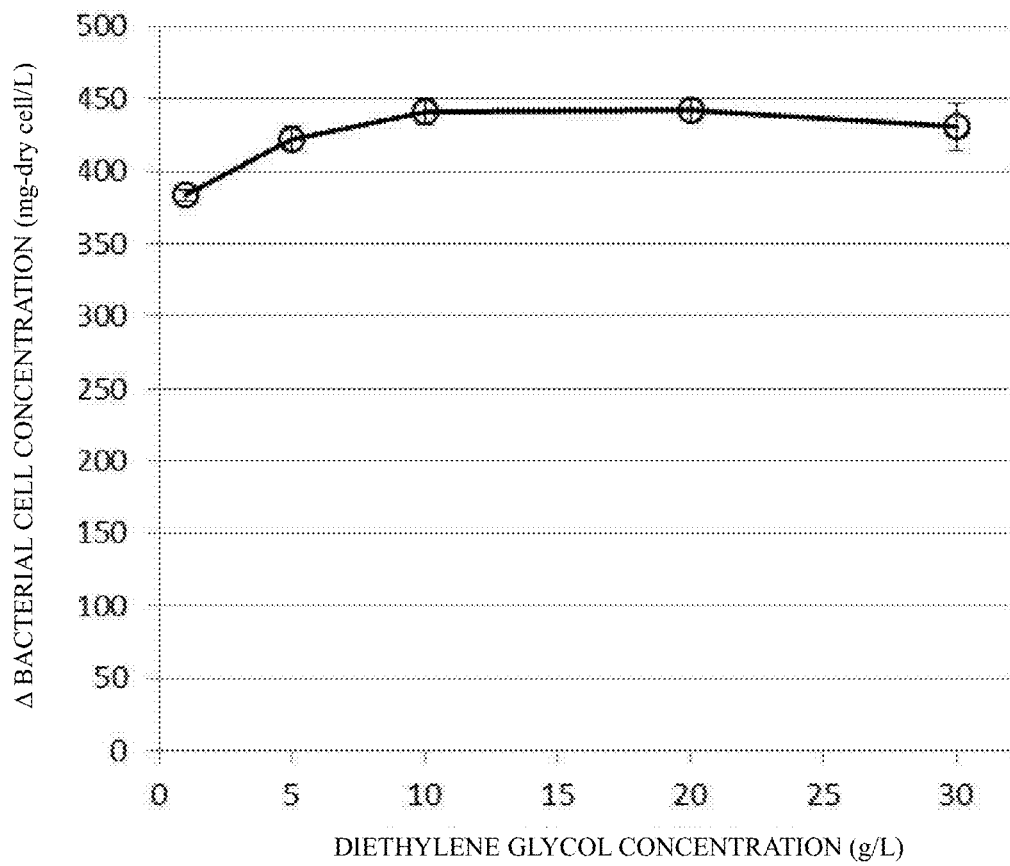

[FIG. 6]
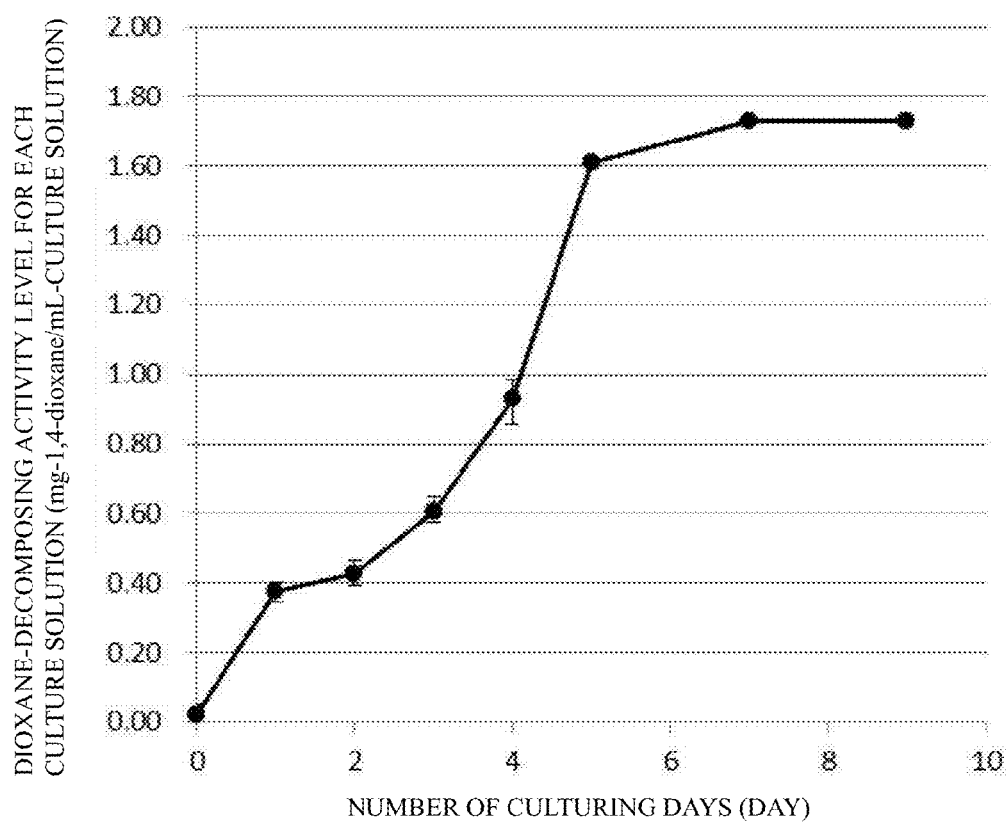

[FIG. 7]
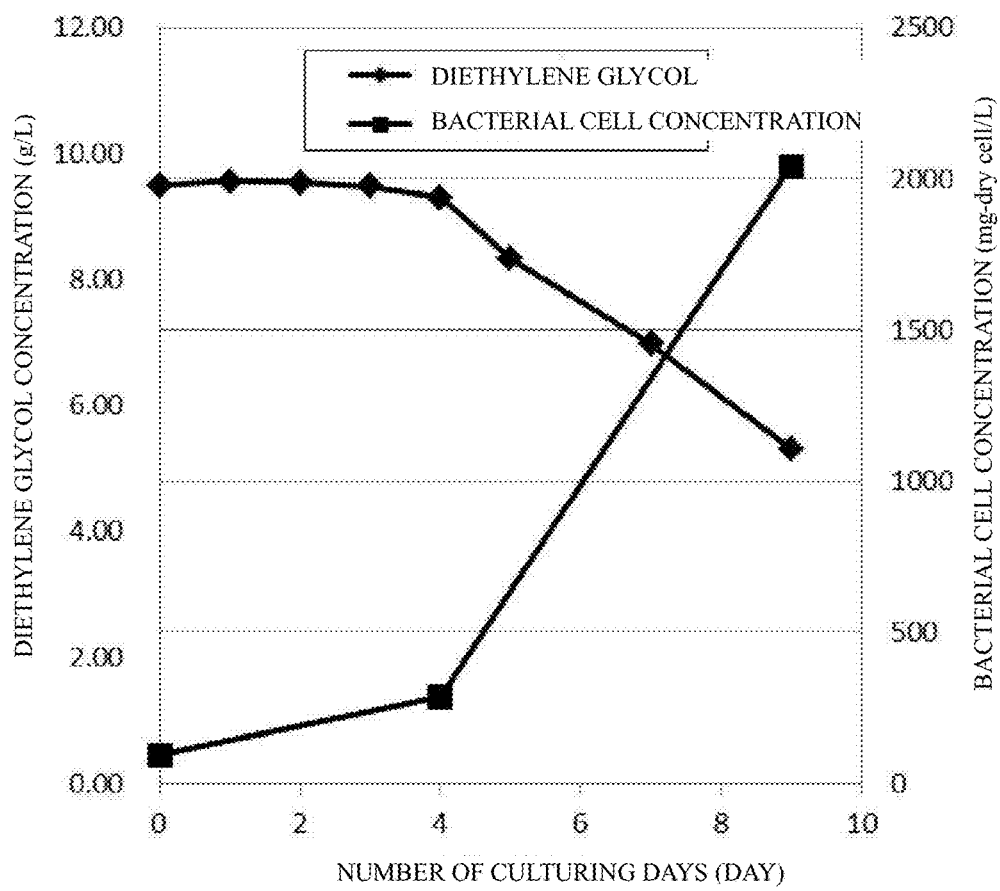
[FIG. 8]
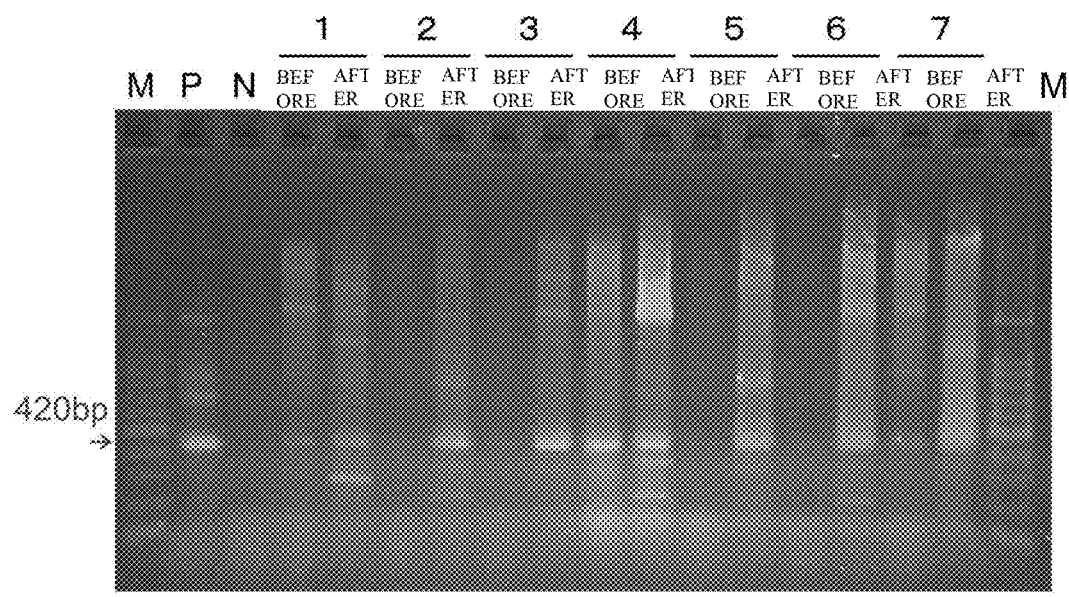

1,4-DIOXANE-DEGRADING BACTERIA CULTURE METHOD, MEDIUM, AND 1,4-DIOXANE TREATMENT METHOD USING 1,4-DIOXANE-DEGRADING BACTERIA

This application is the U.S. National Phase under 35 U.S.C. § 371 of International Application PCT/JP2015/078476, filed Oct. 7, 2015, which claims priority to Japanese Patent Application No. 2014-207776, filed Oct. 9, 2014 and No. 2015-043804, filed Mar. 5, 2015. The International Application was published under PCT Article 21(2) in a language other than English.

TECHNICAL FIELD

The present invention relates to a 1,4-dioxane-degrading bacteria culture method, a medium, and a 1,4-dioxane treatment method using 1,4-dioxane-degrading bacteria.

BACKGROUND ART 1,4-dioxane is a cyclic ether expressed by the following formula (1). 1,4-dioxane is excellent in compatibility with water or organic solvent and is usually used as a reaction solvent for organic synthesis.

[Chem. 1]

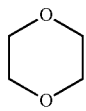
(1)

The manufacturing and import volume of 1,4-dioxane in Japan in 2010 was about 4500 t/year and it is presumed that 1,4-dioxane is released into the environment by about 300 t/year. 1,4-dioxane is water-soluble, and thus 1,4-dioxane diffuses over a wide area when it is released into a water environment. Also, 1,4-dioxane is inferior in volatility, adsorption to solids, photodegradability, hydrolyzability, and biodegradability, and thus it is difficult to be removed from water. Since 1,4-dioxane has acute toxicity and chronic toxicity, and further, carcinogenicity is indicated, the contamination of water environments by 1,4-dioxane is considered to adversely affect humans and animals and plants. Therefore, in Japan, 1,4-dioxane is regulated by a tap water quality standard (0.05 mg/L or less), an environmental standard (0.05 mg/L or less), and a wastewater standard (0.5 mg/L or less).

It is not possible to sufficiently remove 1,4-dioxane from water by conventional treatment methods such as the activated sludge method and the activated carbon adsorption method. The effectiveness of 1,4-dioxane treatment is confirmed only in the advanced oxidation processes using a plurality of physicochemical oxidation methods such as an ozone treatment ($O_3/H_2O_2$) with addition of hydrogen peroxide, an ozone treatment ($O_3$/UV) under ultraviolet irradiation, an ozone treatment under irradiation with radiation or ultrasonic wave in combination. However, the accelerated oxidation method is not widely used due to the high initial cost and running cost. Furthermore, in Non-Patent Literature 1, it is reported that the efficiency of 1,4-dioxane treatment by the accelerated oxidation method decreases when an organic substance other than 1,4-dioxane is present.

There is a demand for a method for treating water containing 1,4-dioxane stably at a low cost, and a biological treatment by 1,4-dioxane-degrading bacteria is proposed in Patent Literature 1 and Non-Patent Literature 2.

1,4-dioxane-degrading bacteria are roughly classified into two groups of bacteria (assimilation bacteria) that can decompose and assimilate 1,4-dioxane as a single carbon source and bacteria (co-metabolizing bacteria) which decomposes 1,4-dioxane by co-metabolic reaction in the presence of other components such as tetrahydrofuran. Assimilation bacteria are further classified into inducible type and constitutive type depending on whether 1,4-dioxane-degrading enzyme is induced by specific substrates or not. In Non-Patent Literatures 3 and 4, it is reported that the THF monooxygenase possessed by these 1,4-dioxane-degrading bacteria are involved in the degradation of 1,4-dioxane. THF monooxygenase is classified as one type of soluble iron (II) monooxygenase (SDIMO) which is responsible for the initial oxidation of various hydrocarbons. Methane/propane monooxygenases and the like are contained in SDIMO (Non-Patent Literature 5). Furthermore, in Non-Patent Literature 6, it is reported that bacteria having SDIMO other than THF monooxygenase can also decompose 1,4-dioxane.

1,4-dioxane-degrading bacteria are extremely slow to proliferate, and when other microorganisms are intermixed, other microorganisms preferentially proliferate. Thus, in order to cultivate 1,4-dioxane-degrading bacteria, it is necessary to sufficiently sterilize the culture apparatus and the medium beforehand so that other bacteria are not intermixed. For sterilization treatment, there are methods such as steam sterilization using an autoclave, dry heat sterilization by heating in an oven or the like, radiation sterilization using gamma rays, and chemical sterilization using ethylene oxide gas. However, since, equipment for sterilization is extremely large scale, energy cost is extremely high, and there is a problem in terms of cost and safety in that the amount of chemicals to be used becomes large, any of the above sterilization methods are difficult to be performed on a large scale. Therefore, it is difficult to supply as much 1,4-dioxane-degrading bacteria as needed at the actual 1,4-dioxane pollution site.

BACKGROUND ART LITERATURE

Patent Literature

Patent Literature 1: Japanese Unexamined Patent Application Publication No. 2008-306939

Non-Patent Literature

Non-patent Literature 1: K. KOSAKA, H. YAMADA, S. MATSUI, and K. SHISHIDA: The effects of the co-existing compounds on the degradation of micropollutants using the ozone/hydrogen peroxide process. Water Sci. Technol., 42, pp. 353-361, 2000.

Non-Patent Literature 2: KAZUNARI SEI, MICHIHIKO IKE: Challenge for biotreatment of groundwater contaminated with 1,4-dioxane by 1,4-dioxane-degrading bacteria, J. Water and Waste, Vol. 53, No. 7, 2011.

Non-Patent Literature 3: H. MASUDA, K. McCLAY, R. J. STEFFAN, and G. J. ZYLSTRA: Biodegradation of tetrahydrofuran and 1,4-dioxane by soluble diiron monooxygenase in *Pseudonocardia* sp. strain ENV478. J. Mol. Microbiol. Biotechnol. 22(5), pp. 312-316, 2012.

Non-Patent Literature 4: A. GROSTERN, C. M. SALES, W.-Q. ZHUANG, O. ERBILGIN, and L. ALVAREZ-COHEN: Glyoxylate metabolism is a key feature of the metabolic degradation of 1,4-dioxane by *Pseudonocardia dioxanivorans* strain CB1190. Appl. Environ. Microbiol., 78(9), pp. 3298-3308, 2012.

Non-Patent Literature 5: N. V. COLEMAN, N. B. BUI, and A. J. HOLMES: Soluble diiron monooxygenase gene diversity in soils, sediments and ethane enrichments. Environ. Microbiol., 8(7), pp. 1228-1239, 2006.

Non-Patent Literature 6: S. MAHENDRA, and L. ALVAREZ-COHEN: Kinetics of 1,4-dioxane biodegradation by monooxygenase-expressing bacteria. Environ. Sci. Technol., 40(17), pp. 5435-5442, 2006.

SUMMARY OF THE INVENTION

Problems to be Solved by the Invention

To provide an effective 1,4-dioxane-degrading bacteria culture method.

Means for Solving the Problems

1) A 1,4-dioxane-degrading bacteria culture method which is characterized in that 1,4-dioxane-degrading bacteria are propagated using a medium containing diethylene glycol at a concentration of 1.0 wt % or more and 10.0 wt/% or less.

2) The culture method disclosed in 1), which is characterized in that the medium is a liquid medium.

3) The culture method disclosed in 1) or 2), which is characterized in that the medium contains at least one of corn steep liquor, casamino acid, yeast extract, and peptone.

4) The culture method disclosed in any one of 1) to 3), which is characterized in that the 1,4-dioxane-degrading bacteria are *Mycobacterium* sp. or *Pseudonocardia* sp.

5) The culture method disclosed in any one of 1) to 4), which is characterized in that the 1,4-dioxane-degrading bacteria are selected from at least one of the groups consisting of *Mycobacterium* sp. D11 (Accession Number: NITE BP-01926), *Pseudonocardia* sp. D17 (Accession Number: NITE BP-01927), and *Pseudonocardia* dioxanivorans CB 1190.

6) The culture method disclosed in any one of 2) to 5), which is characterized in that a continuous culture in which the same amount of culture solution as the supply amount of the liquid medium is taken out while the liquid medium is supplied.

7) A medium which is characterized in that diethylene glycol at a concentration of 1.0 wt % or more and 10.0 wt % or less is contained.

8) The medium disclosed in 7), which is characterized in that the medium is a liquid medium.

9) The medium disclosed in 7) or 8), which is characterized in that the medium contains at least one of corn steep liquor, casamino acids, yeast extract, and peptone.

10) A water treatment method which is characterized in that 1,4-dioxane-degrading bacteria cultured by the culture method disclosed in any one of 1) to 6) are introduced into water containing 1,4-dioxane.

11) The water treatment method disclosed in 10), which is characterized in that diethylene glycol is introduced with the 1,4-dioxane-degrading bacteria.

12) A soil treatment method which is characterized in that 1,4-dioxane-degrading bacteria cultured by the culture method disclosed in any one of 1) to 6) are introduced into soil containing 1,4-dioxane.

13) The soil treatment method disclosed in 12), which is characterized in that diethylene glycol is introduced with the 1,4-dioxane-degrading bacteria.

14) 1,4-dioxane-degrading bacteria which are cultured by the culture method disclosed in any one of 1) to 6).

15) An immobilization carrier which immobilizes the 1,4-dioxane-degrading bacteria disclosed in 14).

16) A 1,4-dioxane treatment method which is characterized in that the proliferation of 1,4-dioxane-degrading bacteria in water or soil containing 1,4-dioxane is promoted by introducing diethylene glycol into the water or the soil containing 1,4-dioxane.

Effects of the Invention 1,4-dioxane-degrading bacteria can be effectively propagated according to the culture method of the present invention. 1,4-dioxane-degrading bacteria can be preferentially propagated even when other microorganisms are present, and since sterilization equipment is not necessary, 1,4-dioxane-degrading bacteria can be propagated in large-scale facilities, and therefore, a large amount of 1,4-dioxane-degrading bacteria required for 1,4-dioxane treatment in sewage treatment plants, factory wastewater treatment facilities, pollution sites, and the like can be supplied. Since 1,4-dioxane treatment can be performed by introducing cultured 1,4-dioxane-degrading bacteria into water or soil, 1,4-dioxane treatment can be performed simply at low cost.

By introducing diethylene glycol into water or soil contaminated with 1,4-dioxane, proliferation properties of degradation bacteria existing in the contaminated environment can be promoted, and the degradation bacteria can be preferentially propagated. Also, the amount of bacterial cells of the degradation bacteria is propagated and thus, 1,4-dioxane treatment by the degradation bacteria can be promoted. Since only diethylene glycol is added, the cost is extremely low. Furthermore, since only the existing degradation bacteria are propagated, it can suppress the influence on the ecosystem.

BRIEF DESCRIPTION OF THE DRAWINGS

FIG. 1 is a flow diagram of contaminated water treatment in standard activated sludge method.

FIG. 2 is a view illustrating proliferation properties in the presence of diethylene glycol in 1,4-dioxane-degrading bacteria.

FIG. 3 is a view illustrating time course of a 1,4-dioxane-degrading activity level in 1,4-dioxane-degrading bacteria.

FIG. 4 is a photograph of reactors in each of which 1,4-dioxane-degrading bacteria are cultured in culture solution containing diethylene glycol (Right) or glucose (Left).

FIG. 5 is a view illustrating the relationship between the concentration of diethylene glycol and the Δ bacterial cell concentration of 1,4-dioxane-degrading bacteria in culture solution.

FIG. 6 is a view illustrating time course change in 1,4-dioxane-degrading activity level during culturing of 1,4-dioxane-degrading bacteria when corn steep liquor is added.

FIG. 7 is a view illustrating time course change in the diethylene glycol concentration and the bacterial cell concentration during culturing of 1,4-dioxane-degrading bacteria when corn steep liquor is added.

FIG. 8 is a view illustrating results of electrophoresis of PCR-amplified product of SDIMO genes before and after culturing (zero days later and six days later) of soil samples 1 to 7 in a liquid medium supplemented with diethylene glycol.

MODE FOR CARRYING OUT THE INVENTION

The details of the present invention are described below.

The present invention is characterized in that 1,4-dioxane-degrading bacteria are propagated using a medium containing diethylene glycol.

Conventionally, in order to increase 1,4-dioxane-degrading bacteria (referred to as "degradation bacteria", hereinafter), sufficient sterilization was necessary to be performed beforehand such that other microorganisms were prevented from being mixed therein.

The present invention is based on an entirely new knowledge that has not been known that degradation bacteria exhibit superior proliferation properties in the presence of diethylene glycol than do other microorganisms. The reason degradation bacteria are excellent in proliferation properties in the presence of diethylene glycol is unknown; however, since degradation bacteria has better ability to utilize diethylene glycol as a carbon source than other microorganisms, it is presumed that degradation bacteria can preferentially grow in the presence of diethylene glycol. Therefore, in the presence of diethylene glycol, degradation bacteria can be propagated even when other microorganisms exist. In other words, in the presence of diethylene glycol, degradation bacteria can be propagated without killing other microorganisms.

Diethylene glycol is glycol expressed by the following formula (2).

[Chem. 2]

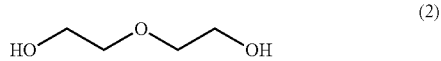

(2)

Diethylene glycol is a highly biodegradable compound which is decomposed in the environment. Many microorganisms present in the environment can use diethylene glycol as a carbon source and decomposition bacteria can also use diethylene glycol as a carbon source. Furthermore, decomposition bacteria are superior in the ability to utilize diethylene glycol as a carbon source, compared with microorganisms not having the ability to decompose dioxane.

Decomposition bacteria are present in nature and can be screened by culturing sludge or the like collected from water or soil contaminated with 1,4-dioxane in a medium containing only 1,4-dioxane as a carbon source. The decomposition bacteria used in the present invention is not particularly limited and bacteria belonging to *Mycobacterium* sp., *Pseudonocardia* sp., *Afipia* sp., *Rhodococcus* sp., *Flavobacterium* sp., *Methylosinus* sp., *Burkholderia* sp *Ralstonia* sp *Cordyceps* sp., *Xanthobacter* sp., *Acinetobacter* sp., or the like can be used.

Dioxane-decomposing bacteria are roughly classified into two species of a bacterium that can decompose and assimilate 1,4-dioxane as a single carbon source and a bacterium that decomposes 1,4-dioxane by co-metabolic reaction in the presence of other components such as tetrahydrofuran. The decomposition bacteria used in the present invention is not particularly limited and it is preferable that *Mycobacterium* sp. D11, *Pseudonocardia* sp. D17, *Mycobacterium* sp. D6, *Pseudonocardia* dioxanivorans CB1190, *Afipia* sp. D1, *Mycobacterium* sp. PH-06, *Pseudonocardia* benzenivorans B5, *Flavobacterium* sp., *Pseudonocardia* sp. ENV478, *Pseudonocardia* tetrahydrofuranoxydans K1, *Rhodococcus* ruber T1, *Rhodococcus* ruber T5, *Methylosinus trichosporium* OB3b, *Mycobacterium* vaccae JOB5, *Burkholderia cepacia* G4, *Pseudomonas mendocina* KR1, *Pseudonocardia* tetrahydrofuranoxydans K1, *Ralstonia pickettii* PKO1, *Rhodococcus* sp. RR1, *Acinetobacter Baumannii* DD1, *Rhodococcus* sp. 219, *Pseudonocardia antarctica* DVS 5a1, *Cordyceps sinesis* A, *Rhodococcus aetherivorans* JCM14343, or the like be used. It is preferable that *Pseudonocardia* sp. D17, *Mycobacterium* sp. D11, or *Pseudonocardia dioxanivorans* CB 1190 of those described above be used because they have relatively high decomposition properties of 1,4-dioxane.

*Mycobacterium* sp. D11 and *Pseudonocardia* sp. D17 have been internationally deposited on Aug. 29, 2014 at the National Institute of Technology and Evaluation, Patent Microorganisms Depositary Center (NPMD) (Kazusa Kamatari 2-5-8, Kisarazu city, Chiba Prefecture, Japan (postal code 292-0818)) as accession number NITE BP-01926 and accession number NITE BP-01927, respectively.

*Pseudonocardia dioxanivorans* CB1190 (referred to as strain CB1190, hereinafter) can be purchased from the United States ATCC (ATCC 55486). In addition to ATCC in the United States, it can also be purchased at JCM (Institute of Physical and Chemical Research, Bioresource Center, Microbial Material Development Office) and DSM in Germany.

*Rhodococcus aetherivorans* JCM 14343 can be purchased from JCM (Institute of Physical and Chemical Research, Bioresource Center, Microbial Material Development Office) (JCM 14343). Further, it can also be purchased at DSM in Germany, NCIMB in the United Kingdom and CIP in France.

The condition for increasing decomposition bacteria is not particularly limited as long as it is in an environment where diethylene glycol is present. Examples thereof include liquid medium and solid medium. Also, sterilization may not be performed and other microorganisms may be present. The medium is not particularly limited as long as it is capable of culturing the decomposition bacteria, and a known medium such as an MGY medium and a CGY medium to which diethylene glycol is added can be used.

It is preferable that a liquid medium be used to increase the amount of decomposition bacteria to a large extent and it is further preferable that the 1,4-dioxane-decomposing bacteria be propagated by continuous culture in which culture solution containing decomposition bacteria is collected in an amount which is the same as the supply amount of liquid medium while the liquid medium is supplied.

The concentration of diethylene glycol when degradation bacteria are propagated is not particularly limited. However, in the case of liquid medium, it is preferable that the concentration of diethylene glycol be set to be 0.01 mg/L or more and 100 g/L or less ($1.0 \times 10^{-8}$ wt % or more and 10.0 wt % or less). It is more preferable that the lower limit of the concentration of diethylene glycol in the liquid medium be set to be 1 g/L or more (0.1 wt % or more), it is even more preferable to be 5 g/L or more (0.5 wt % or more), and it is most preferable to be 10 g/L or more (1.0 wt % or more). It is more preferable that the upper limit of the concentration of diethylene glycol be set to be 60 g/L or less (6.0 wt % or less), it is even more preferable to be 30 g/L or less (3.0 wt % or less), and it is most preferable to be 20 g/L or less (2.0 wt % or less). Also, in the case of a solid medium, it is preferable to be 0.1 wt % or more and 10.0 wt % or less. It is more preferable that the lower limit of the concentration of diethylene glycol in the solid medium be set to be 1.0 wt % or more, it is more preferable to be 1.5 wt % or more, and it is most preferable to be 2.0 wt % or more. It is more preferable that the upper limit of the concentration of tdiethylene glycol be set to be 9.0 wt % or less, it is even more preferable to be 8.0 wt % or less, and it is most preferable to be 7.0 wt % or less.

When the degradation bacteria are propagated, inorganic substances and organic substances necessary for activities of degradation bacteria can be added. Since the amount of microbial activity is limited by a factor which has the lowest quantity among factors such as necessary nutrients, proliferation can be promoted by adding deficient nutrients. Inorganic substances to be added are not particularly limited, and examples thereof include $K_2HPO_4$, $(NH_4)_2SO_4$, $MgSO_4 \cdot 7H_2O$, $FeCl_3$, $CaCl_2$, NaCl, and the like.

Organic substances to be added are not particularly limited. However, it is preferable that corn steep liquor, casamino acid, yeast extract, or peptone be used. The growth rate of degradation bacteria can be propagated by adding organic substances other than diethylene glycol. It is preferable that the weight ratio of diethylene glycol to the organic substances to be added other than diethylene glycol be set to be in the range of 60:40 to 99:1, it is more preferable that the weight ratio be set to be in the range of 70:30 to 98:2, it is even more preferable that the weight ratio be set to be in the range of 75:25 to 95:5, and it is most preferable that the weight ratio be set to be in the range of 80:20 to 90:10.

It is preferable that the culturing of degradation bacteria be carried out at 15° C. to 45° C. It is more preferable that the culturing of degradation bacteria be carried out at 20° C. to 40° C. and it is most preferable that the culturing of degradation bacteria be carried out at 25° C. to 35° C. Also, it is preferable that the value of pH be set to be in the range of 5 to 8 and it is more preferable that the value of pH be set to be in the range of 6 to 8. The culture time is not particularly limited as long as the necessary amount of bacterial cells can be obtained. When degradation bacteria are propagated in a closed system, it is preferable that it be performed for three to thirty days.

In the culture method of the present invention, degradation bacteria can be propagated without killing other microorganisms and a sterilizing apparatus is unnecessary. Therefore, it is easy to culture the degradation bacteria on a large scale and it is possible to supply a large amount of bacterial cells necessary for 1,4-dioxane treatment in sewage treatment plants, factory wastewater treatment facilities, contaminated soil treatment sites, and the like.

Dioxane-degrading bacteria can be used for 1,4-dioxane treatment in any form such as bacterial cells filtered out from the culture solution, frozen and preserved bacterial cells, L-drying preserved bacterial cells, lyophilized bacterial cells, an immobilization carrier in which dioxane-degrading bacteria are immobilized in a resin or the like, or suspension containing dioxane-degrading bacteria such as culture solution and concentrate thereof.

Cultured degradation bacteria are introduced into water contaminated with 1,4-dioxane and the environment is set to be an aerobic state, in such a manner that 1,4-dioxane biological treatment by degradation bacteria can be carried out. Water such as sewage and industrial wastewater often contains nutrient salts such as $K_2HPO_4$, $(NH_4)_2SO_4$, $MgSO_4 \cdot 7H_2O$, $FeCl_3$, $CaCl_2$, and NaCl. However, if the concentration of the nutrient salts is low, 1,4-dioxane treatment by metabolism/utilization of degradation bacteria can be promoted by introducing the necessary amount of nutrient salts. Also, 1,4-dioxane-degrading activity of degradation bacteria can be maintained even in water containing other microorganisms by introducing diethylene glycol along with degradation bacteria. It should be noted that since diethylene glycol is excellent in biodegradability and is quickly degraded in the environment, the load on the environment by diethylene glycol is extremely small.

It is preferable that the concentration of diethylene glycol in the contaminated water be set to be $1.0 \times 10^{-8}$ wt % or more and 10.0 wt % or less. It is more preferable that the lower limit of the concentration of the diethylene glycol be set to be 0.1 wt % or more, it is more preferable to be 0.5 wt % or more, and it is most preferable to be 1.0 wt % or more. It is more preferable that the upper limit of the concentration of the diethylene glycol be set to be 6.0 wt % or less, it is even more preferable to be 3.0 wt % or less, and it is most preferable to be 2.0 wt % or less.

FIG. 1 is a flow diagram of contaminated water treatment in a conventional activated sludge process using an aeration tank. In the standard activated sludge method, biological treatment by useful microorganisms is carried out in an aeration tank. In the aeration tank, an aeration tube is arranged and bubbles are supplied from a diffusing tube to the water in the aeration tank. Oxygen is dissolved from the bubbles in the water and organic matter is treated by metabolism/utilization by useful microorganisms. Since the aeration tank is in an aerobic environment, 1,4-dioxane contained in contaminated water can be treated simply by introducing degradation bacteria into the aeration tank. In FIG. 1, a flow of introducing culture solution containing degradation bacteria is illustrated. However, culture solution collected by continuous culture may be continuously introduced. Also, instead of culture solution, introduced may be: the degradation bacteria filtered out from the culture solution or the like without change or in the form of frozen and preserved bacterial cells, L-drying-preserved bacterial cells, lyophilized bacterial cells, or an immobilization carrier in which the degrading bacteria are immobilized in a resin or the like, or a suspension obtained by concentrating the culture solution, or the like.

Cultivated degradation bacteria are simply introduced into the aeration tank, in such a manner that 1,4-dioxane treatment can be carried out, so that the equipment used in the conventional standard activated sludge method can be used as it is. In the culture method of the present invention, facilities and chemicals for sterilization treatment are unnecessary, so that both the initial cost and the running cost can be reduced. Therefore, the biological treatment method by degradation bacteria cultured by the culture method of the present invention is lower in cost, compared with the accelerated oxidation method using a plurality of oxidizing agents. Also, since a commercially available culture device can also be used without change, the cost is low.

1,4-dioxane can be treated by introducing the cultivated degradation bacteria into the soil contaminated with 1,4-dioxane. The conventional soil treatment method requires enormous labor and cost, such as construction of field plants, excavation of soil, detoxification, and backfilling. However, in the method of the present invention, 1,4-dioxane can be biologically treated simply by introducing degradation bacteria into the soil. Generally, since nutrients are insufficient in the soil, it is preferable that diethylene glycol be introduced into the soil along with degradation bacteria. Also, either or both of inorganic substances such as $K_2HPO_4$, $(NH_4)_2SO_4$, $MgSO_4 \cdot 7H_2O$, $FeCl_3$, $CaCl_2$, and NaCl, and organic substances such as corn steep liquor, casamino acid, yeast extract, peptone may be introduced.

It is preferable that the concentration of diethylene glycol added be such that the contaminated soil becomes 0.1 wt % or more and 10 wt % or less. It is more preferable that the lower limit of the concentration of the diethylene glycol be set to be 1.0 wt % or more, it is more preferable to be 1.5 wt % or more, and it is most preferable to be 2 wt % or more. It is more preferable that the upper limit of the concentration of the diethylene glycol be set to be 9.0 wt % or less, it is more preferable to be 8.0 wt % or less, and it is most preferable to be 7.0 wt % or less.

As described above, degradation bacteria exist in nature. The proliferation of degradation bacteria existing in nature can be promoted by introducing diethylene glycol into water or soil contaminated with 1,4-dioxane and degradation bacteria can be preferentially propagated. As the amount of bacterial cells of the degradation bacteria is propagated, 1,4-dioxane treatment by degradation bacteria is promoted. It is only necessary to add diethylene glycol and it is not necessary to culture degradation bacteria, and thus the cost is extremely low. Also, it increases only the existing degradation bacteria and it does not introduce new degradation bacteria, and thus the influence on the ecosystem can be reduced.

In this case, it is preferable that diethylene glycol introduced so that the concentration of diethylene glycol in contaminated water or contaminated soil becomes $1.0 \times 10^{-8}$ wt % or more and 10.0 wt % or less. It is more preferable that the lower limit of the concentration of diethylene glycol be set to be 0.1 wt % or more, it is more preferable to be 0.5 wt % or more, and it is most preferable to be 1.0 wt % or more. It is more preferable that the upper limit of the concentration of diethylene glycol be set to be 9.0 wt % or less, it is even more preferable to be 8.0 wt % or less, and it is most preferable to be 7.0 wt % or less.

It should be noted that degradation bacteria inhabiting a contaminated environment or other degradation bacteria may be cultured and introduced with diethylene glycol.

Next, details of the present invention are described based on examples. However, the present invention is not limited thereto.

EXAMPLES

Example 1

Strain CB1190, strain D11, and strain D17 were used as 1,4-dioxane-degrading bacteria. Each degradation bacterium was cultured for ten days using a CGY medium (casitone: 5 g/L, glycerin: 5 g/L, yeast extract: 1 g/L) containing 1,4-dioxane at a concentration of 500 mg/L. After cultivation, the bacterial cells were harvested and washed with a centrifugal separator, and then mixed with 20 mL of physiological saline, in such a manner that an inoculum suspension was obtained. It should be noted that an inoculum suspension (OD600: approximately 10) which was turbidity-standardized using a spectrophotometer was used as the inoculum suspension.

A liquid medium (medium composition: $K_2HPO_4$: 1 g/L, $(NH_4)_2SO_4$: 1 g/L, NaCl: 50 mg/L, $MgSO_4.7H_2O$: 200 mg/L, $FeCl_3$: 10 mg/L, $CaCl_2$: 50 mg/L, pH: 7.3) was added to an Erlenmeyer flask equipped with baffles with a volume of 300 mL by 100 mL, and then, sterilization was performed with an autoclave. Next, diethylene glycol solution having a predetermined concentration was added so that the concentration became 1 g/L, and then 1 mL of the inoculum suspension was added and the rotary shaking culture was performed at 28° C. and 120 rpm for nine days.

The bacterial cells in the culture solution were collected as filtrate by suction filtration after the culture was finished. Then, the filtrate was dried at 105° C. overnight, and the weight of the bacterial cells was measured, in such a manner that the bacterial cell concentration (mg-dry cell/L) was obtained. Proliferation of the bacterial cells was evaluated by Δ bacterial cell concentration obtained by subtracting the initial bacterial cell concentration from the bacterial cell concentration on the ninth day of culture.

FIG. 2 is a view illustrating proliferation properties of each degradation bacterium in the presence of diethylene glycol. The concentrations of the bacterial cells increased in all degradation bacteria and it was confirmed that degradation bacteria could grow using diethylene glycol as a carbon source. Especially, strain D17 showed extremely high proliferation properties.

Example 2

Strain D17 was cultured in an MGY medium (Malt Extract: 10 g/L, glucose: 4 g/L, Yeast Extract: 4 g/L) for two weeks.

Ammonium hydroxide and dipotassium hydrogenphosphate were added to pollution site groundwater (pH: 7.38, 1,4-dioxane: 0.16 mg/L, phosphate ion: 0.08 mg/L, total nitrogen: 36.5 mg/L, total organic carbon content: 11 mg/L, chemical oxygen required amount: 33 mg/L) containing 1,4-dioxane such that the concentrations respectively became 1 g/L. Then, diethylene glycol was added so that the concentration became 20 g/L, in such a manner that a culture solution was prepared.

The culture solution of 650 mL was added to a reactor having a volume of 1 L, and strain D17 (bacterial cell concentration: 157 mg-dry cell/L) was added, and then the solution was cultured for six days. During culturing, the temperature and the pH were controlled to be 28° C. and 7.0 and aeration at 0.65 L/min was performed.

Comparative Example 1

Degradation bacteria were cultured in the same manner as in Example 2 except that diethylene glycol was replaced with glucose.

[1,4-Dioxane-Degrading Activity Level Measurement 1]

The culture solutions of Example 2 and Comparative Example 1 were respectively sampled by 1 mL, and 1,4-dioxane-degrading activity level of the samples was measured. Sampling was carried out immediately after the start of culturing and on the first to sixth days from the start of culturing. The method for measuring the degradation activity level is as follows.

A liquid medium (medium composition: $K_2HPO_4$: 1 g/L, $(NH_4)_2SO_4$: 1 g/L, NaCl: 50 mg/L, $MgSO_4.7H_2O$: 200 mg/L, $FeCl_3$: 10 mg/L, $CaCl_2$: 50 mg/L, pH: 7.3) containing 1,4-dioxane of 100 mg/L and the sampled culture solution were added to an Erlenmeyer flask with baffles with a volume of 100 mL by 19 mL and 1 mL, respectively, and then the rotary shaking culture was performed at 28° C. and 120 rpm for 24 hours. It should be noted that three Erlenmeyer flasks in total were prepared in which the tests by the same procedure were carried out.

The concentration of 1,4-dioxane in the solution after culturing was finished was measured with a headspace gas chromatograph mass spectrometer (Shimadzu Corporation: GC/MS-QP2010 PLUS, TURBOMATRIX HS40). Also, a blank sample to which the culture solution was not added was also tested by the same procedure and the degradation activity level of 1,4-dioxane was determined by the following equation. In this measurement method, the degradation activity level represents the amount of 1,4-dioxane decomposed by the culture solution of 1 ml for 24 hours. The arithmetic mean (n=3) of the measurement results is shown in FIG. 3. Also, a photograph of the reactor on the third day of culturing is illustrated in FIG. 4. In FIG. 4, the right side shows Example 2 using diethylene glycol and the left side shows the comparative example 1 using glucose.

1,4-dioxane-degrading activity level (mg-1,4-Dioxane/mL-culture solution)=(C0−C24)×20 mL/1000 mL C0 (mg/L): 1,4-dioxane concentration after a blank sample to which no culture solution was added was subjected to the rotary shaking culture for 24 hours.

C24 (mg/L): 1,4-dioxane concentration after the sample to which the culture solution was added was subjected to the rotary shaking culture for 24 hours.

In Example 2 where diethylene glycol was used as a carbon source, the degradation activity level which was 0.04 immediately after the start of culturing increased with the passage of days, and increased to 1.63 on the sixth day of culturing. Other microorganisms which inhabited the pollution site groundwater were not killed because they were not subjected to sterilization treatment such as heating. However, the degradation activity increased, and thus it became clear that strain D17 preferentially grew in the presence of diethylene glycol. Also, as shown in FIG. 4 (right), the culture medium on the third day of culturing was slightly turbid but had transparency.

Although, in Comparative Example 1 where glucose was used as a carbon source, the degradation activity level during the culturing period changed in the range of 0.15 to 0.29 and no increase in degradation activity was observed. This was because strain D17 was inferior in its ability to utilize glucose to other microorganisms present in the pollution site groundwater, and thus strain D17 could not grow. Additionally, the culture solution gradually started to become turbid and the culture solution on the third day became markedly opaque as shown in FIG. 4 (left). This was because the other microorganisms preferentially grew.

In terms of degradation activity level on the sixth day of culturing, the level was 1.63 in Example 2 and 0.20 in Comparative Example 1. The degradation activity level in Example 2 was eight times more superior than that of Comparative Example 1. This is considered to be due to the fact that strain D17 was superior in ability to utilize diethylene glycol as a carbon source compared with the other microorganisms and the amount of bacterial cells of strain D17 had propagated.

Example 3

100 mL of a liquid medium (medium composition: $K_2HPO_4$: 1 g/L, $(NH_4)_2SO_4$: 1 g/L, NaCl: 50 mg/L, $MgSO_4 \cdot 7H_2O$: 200 mg/L, $FeCl_3$: 10 mg/L, $CaCl_2$: 50 mg/L, pH: 7.3) containing diethylene glycol of 1 g/L was added to an Erlenmeyer flask equipped with baffles with a volume of 300 mL. Next, strain D17 which was inoculated in the MGY medium in advance was cultured (initial bacterial cell concentration: 111 mg-dry cell/L) and was subjected to the rotary shaking culture at 28° C. and 120 rpm for seven days.

Example 4

Degradation bacteria were cultured in the same manner as in Example 3 except that the concentration of diethylene glycol in the liquid medium was set to be 5 g/L.

Example 5

Degradation bacteria were cultured in the same manner as in Example 3 except that the concentration of diethylene glycol in the liquid medium was set to be 10 g/L.

Example 6

Degradation bacteria were cultured in the same manner as in Example 3 except that the concentration of diethylene glycol in the liquid medium was set to be 20 g/L.

Example 7

Degradation bacteria were cultured in the same manner as in Example 3 except that the concentration of diethylene glycol in the liquid medium was set to be 30 g/L.

[Bacterial Body Concentration Measurement]

The bacterial cells in the culture solution were collected as a filter residue through suction filtration after the cultivation was finished and the bacterial cells were dried at 105° C. overnight, and then the weight of the collected bacterial cells was measured. The bacterial cell concentration (mg-dry cell/L) was obtained from the value of the measured bacterial cell weight. It should be noted that in each example, two similarly tested samples were prepared and the average value thereof was set to the bacterial cell density. The proliferation property of the bacterial cells was evaluated by Δ bacterial cell concentration which was obtained by subtracting the initial bacterial cell concentration from the bacterial cell concentration on the seventh day of culturing. FIG. 5 shows the Δ bacterial cell concentration.

The bacterial cell concentration increased as the concentration of diethylene glycol increased from 1 g/L to 10 g/L. In Examples 5 to 7 in which the concentration of diethylene glycol was in the range of 10 g/L to 30 g/L, the bacterial cell concentration hardly changed even when the concentration of diethylene glycol was increased. As a result of measuring the pH after cultivation in Examples 5 to 7 was finished, the pH was in the range of 3.42 to 3.91 and it is presumed that proliferation was inhibited by the decrease in pH, and thus the bacterial cell concentrations became roughly the same.

Example 8

Ammonium sulfate and dipotassium hydrogenphosphate were respectively added to pollution site groundwater containing 1,4-dioxane used in Example 2 such that the concentrations thereof became 1 g/L. Then, diethylene glycol solution of a predetermined concentration was added such that the concentration became 10 g/L, in such a manner that the culture solution was prepared.

The culture solution of 8 L was added to a reactor of a capacity of 10 L, and then strain D17 (concentration of the initial bacterial cells: 43.2 mg-dry cell/L) was added and cultured at 28° C. for nine days while the aeration was performed at 4 L/min. Also, on the fourth day of culturing, corn steep liquor was added only once such that the concentration became 5 g/L. It should be noted that during the culture period, the pH was controlled to be in the range of 7.0±0.2.

[1,4-Dioxane-Degrading Activity Level Measurement 2]

A sample of 1 mL was obtained from the culture solution and 1,4-dioxane-degrading activity level was measured in the same manner as "1,4-dioxane-degrading Activity Level Measurement 1" above. Sampling was carried out immediately after the start of culturing and on the first, second, third, fourth, fifth, seventh, and ninth day after starting the culture. The sampling on the fourth day was carried out immediately before CSL was added. The measurement results are illustrated in FIG. 6.

[Measurement of Concentration of Diethylene Glycol]

The concentration of diethylene glycol in the culture solution subjected to sampling in "1,4-dioxane-degrading Activity Level Measurement 2" above was measured using a high performance liquid chromatography (Waters Alliance 2695 detector: RID).

[Measurement of Bacterial Cell Concentration]

The culture solution was subjected to sampling immediately after the start of culture and on the fourth day and ninth day from the start of culture by 150 mL, respectively, and 100 mL was accurately collected from each sample with a measuring cylinder, and then all the bacterial cells were collected and cleaned through suction filtration and the sample was dried at 105° C. overnight. It should be noted that the sampling on the fourth day was carried out immediately before the corn steep liquor was added. Thereafter, the dry weight was measured and calculated as the bacterial cell concentration.

The concentration of diethylene glycol and the time course change in bacterial cell concentration are illustrated in FIG. 7.

The degradation activity level immediately after culturing was as low as 0.02. However, the degradation activity level on the first day of culturing increased to 0.38 and increased to 0.93 on the fourth day of culturing. The degradation activity level on the fifth day of culturing, which was 24 hours after corn steep liquor was added, greatly increased to 1.61 and the degradation activity level on the seventh day and the ninth day was 1.73. Although the degradation activity level after the seventh day actually further increased, it could not be calculated as an accurate activity value because 1,4-dioxane concentration dropped below the limit of quantification. From this, it was confirmed that the degradation activity of 1,4-dioxane was enhanced by adding corn steep liquor. It should be noted that in this test method, the charged concentration of 1,4-dioxane was 100 mg/L and the upper limit of the degradation activity value in consideration of reduction in a blank sample was about 1.73.

The concentration of diethylene glycol gradually decreased from the start of the test to the fourth day. The concentration of diethylene glycol decreased rapidly after the fourth day of culturing and it was confirmed that the utilization rate of diethylene glycol, that is, the proliferation rate of degradation bacteria, increased by adding corn steep liquor.

The concentration of bacterial cells was 94 mg-dry cell/L on the zeroth day of culturing and was 288 mg-dry cell/L on the fourth day. However, the concentration of bacterial cells increased to 2043 mg-dry cell/L on the ninth day of culturing. Therefore, it became clear that the culture solution containing degradation bacteria at a high concentration could be obtained by adding an organic substance other than diethylene glycol.

Example 9

The proliferation of SDIMO-bearing bacteria by culturing in a medium supplemented with diethylene glycol was investigated in seven types of soil collected from different places at sites contaminated with 1,4-dioxane. It should be noted that the proliferation of SDIMO-bearing bacteria was evaluated by an increase in PCR amplification products of about 420 bp derived from a SDIMO-encoding gene (a SDIMO gene).

The soil with a wet weight of 10 g was added to an Erlenmeyer flask of 300 ml in which the liquid medium of 90 ml (medium composition: $K_2HPO_4$: 1 g/L, $(NH_4)_2SO_4$: 1 g/L, NaCl: 50 mg/L, $MgSO_4 \cdot 7H_2O$: 200 mg/L, $FeCl_3$: 10 mg/L, $CaCl_2$: 50 mg/L, pH: 7.0) was placed. Then, diethylene glycol was added such that the final concentration became 20 g/L and the rotary shaking culture was carried out at 28° C. and 120 rpm.

The samples were collected immediately after diethylene glycol was added and after six days by 5 ml, respectively, and a supernatant was removed by centrifugation (10,000×g, 4° C., 5 min), and then DNA was recovered from the soil of 0.5 g (of wet weight). For DNA extraction, a soil DNA extraction kit (manufactured by Nippon Gene Co., Ltd., product name: ISOIL for Beads Beating) was used and the extracted DNA was purified using a DNA fragment purification kit (Toyobo Co., Ltd., product name: MagExtractor-PCR & Gel Clean up-).

Detection of the SDIMO gene was carried out by PCR using the primer set [NVC57, NVC66] described in Non-Patent Literature 5 mentioned above. When the SDIMO gene was present in a sample, a PCR amplification product of about 420 bp was specifically amplified by PCR using the primer set. PCR reaction system was set to 50 μl (SapphireAmp Fast PCR Master Mix (Takara Bio Inc.) 25 μl, each primer 0.5 μM, DNA 1 μl, diluting sterile ultrapure water in measuring cylinder to 50 μl total). PCR amplification was performed after thermal denaturation was carried out at 94° C. for five minutes and 35 cycles each of which constituted heat denaturation at 94° C. for 30 seconds, annealing at 57° C. for 30 seconds, and extension at 72° C. for 1 minute was repeatedly performed. Finally, extension was performed at 72° C. for five minutes. Samples after PCR was performed were subjected to electrophoresis (100 V, 30 min) using the agarose gel of 1.5% and were stained with SYBR Green I for fifteen minutes, and then ultraviolet rays were irradiated to examine the presence or absence and the strength of the PCR amplification product of about 420 bp. FIG. 8 illustrates the results of PCR amplification of SDIMO genes before and after (day zero and after six days) culturing of soil samples 1 to 7 in a liquid medium supplemented with diethylene glycol. It should be noted that in FIG. 8, the lane denoted by M is a DNA ladder marker (product name: 100 bp DNA ladder, manufactured by Takara Bio Inc.), the lane denoted by P is DNA of *Pseudonocardia* sp. D17 which is a 1,4-dioxane utilization bacterium, and the lane denoted by N is a negative control without DNA.

In most cases, only a very small amount of the PCR amplification product of about 420 bp was detected in the soil before culturing was performed. On the other hand, the PCR amplification product of about 420 bp was clearly detected in all samples in the soil after culturing was performed. When the amounts of the PCR amplification products of about 420 bp before and after culturing was performed were compared to each other, it was confirmed that the amount of the amplified product markedly increased after culturing was performed except for the soil sample 4 in which the amount of the amplified product was large before culturing was performed. From the above results, it could be confirmed that culturing with diethylene glycol preferentially proliferated SDIMO-bearing bacteria which were very slightly present in the soil. In other words, indigenous degradation bacteria existing in contaminated environments can be preferentially increased by introducing diethylene glycol into water or soil contaminated with 1,4-dioxane, and thus it was confirmed that degradation in 1,4-dioxane treatment could be promoted by increasing the amount of bacterial cells of degradation bacteria.

What is claimed is:

1. A 1,4-dioxane-degrading bacteria culture method comprising culturing/incubating 1,4-dioxane-degrading bacteria with a medium containing diethylene glycol at a concentration of 1.0 wt % or more and 10.0 wt % or less, thereby multiplying the 1,4-dioxane-degrading bacteria, wherein the 1,4-dioxane-degrading bacteria are at least one of *Mycobacterium* sp. D11 (Accession Number: NITE BP-01926) or *Pseudonocardia* sp. D17 (Accession Number: NITE BP-01927).

2. The culture method according to claim 1, wherein the medium is a liquid medium.

3. The culture method according to claim 2, wherein the 1,4-dioxane-degrading bacteria are cultured/incubated with the liquid medium, obtaining culture solution, wherein the same amount of culture solution as the supply amount of liquid medium is removed while the liquid medium is supplied.

4. The culture method according to claim 2, wherein the medium contains at least one component selected from the group consisting of corn steep liquor, casamino acid, yeast extract, and peptone.

5. The culture method according to claim 1, wherein the medium contains at least one component selected from the group consisting of corn steep liquor, casamino acid, yeast extract, and peptone.

6. The culture method according to claim 5, wherein the 1,4-dioxane-degrading bacteria are cultured/incubated with the liquid medium, obtaining culture solution, wherein the same amount of culture solution as the supply amount of liquid medium is removed while the liquid medium is supplied.

* * * * *